United States Patent [19] [11] 3,959,457

Speaker et al. [45] May 25, 1976

[54] MICROPARTICULATE MATERIAL AND METHOD OF MAKING SUCH MATERIAL

[75] Inventors: Tully J. Speaker, Philadelphia, Pa.; Lawrence J. Lesko, Houston, Tex.

[73] Assignee: Temple University, Philadelphia, Pa.

[22] Filed: Feb. 8, 1973

[21] Appl. No.: 330,476

Related U.S. Application Data

[63] Continuation-in-part of Ser. No. 43,925, June 5, 1970, abandoned.

[52] U.S. Cl. .......... 424/19; 252/301.1 R; 252/316; 424/1; 424/22; 424/32; 424/34; 424/35; 424/257; 427/3; 264/4

[51] Int. Cl.[2] .......... A61K 9/52; B01J 13/02

[58] Field of Search .......... 252/316; 117/100 A; 424/19, 22, 34, 35; 264/4; 106/208, 186, 205, 197 C; 260/209 R

[56] References Cited

UNITED STATES PATENTS

| | | | |
|---|---|---|---|
| 2,386,157 | 10/1945 | Barthen et al. | 117/100 A X |
| 2,688,598 | 9/1954 | McNeely | 260/209 R X |
| 2,947,645 | 8/1960 | Milne | 106/197 C X |
| 3,043,782 | 7/1962 | Jensen | 252/316 |
| 3,265,630 | 8/1966 | Jensen | 252/316 |

FOREIGN PATENTS OR APPLICATIONS

| | | | |
|---|---|---|---|
| 1,091,077 | 11/1967 | United Kingdom | 252/316 |
| 1,091,078 | 11/1967 | United Kingdom | 252/316 |

*Primary Examiner*—Richard D. Lovering
*Attorney, Agent, or Firm*—Paul & Paul

[57] ABSTRACT

In a finely dispersed emulsion of a water immiscible solution of an organic polyfunctional Lewis base and an aqueous solution of a partially hydrophilic, partially lipophilic polyfunctional Lewis acid, a reaction occurs at the phase interface to produce a novel microparticulate material comprised of the reaction product of the Lewis acid and the Lewis base. The maximum particle size dimensions of the microparticulate material depends on the degree of dispersion in the emulsified reaction mixture and may be as low as 2 microns or smaller.

10 Claims, No Drawings

MICROPARTICULATE MATERIAL AND METHOD OF MAKING SUCH MATERIAL

BACKGROUND

This is a continuation-in-part of our application Ser. No. 43,925, filed June 5, 1970, of common assignment herewith and now abandoned.

This invention pertains to a novel microparticulate material, the particles of which are sometimes referred to as microspheroids, and to a method for making such material. More specifically, this invention pertains to a microparticulate material which may serve as a carrier for diffusible reactants such as pharmaceuticals and which therefore constitute a new form of sustained release medicaments.

Microparticulate material which acts as a carrier of other material is fairly well known. Such materials have been used for example in carbon paper and in pharmaceutical preparations. However, the microparticulate material heretofore available has generally acted as a carrier by entrapping within each particle a material, the release of which could be obtained only by crushing or digesting the shell-like particle surrounding it. Moreover, these particles were generally of a minimum particle size of substantially more than 7 microns which therefore limited their use as pharmaceuticals in that they could not be injected intravenously. Further problems with the known prior art microparticulate material arise from the fact that generally such material tends to agglomerate thus deleteriously affecting certain important properties of these materials such as dispersibility.

Another type of cellular particulate material is that disclosed in British Pat. Nos. 1,091,077 and 1,091,078 both of Pilot et al. This material is a polymeric resin, however, and is thought to be generally of such high molecular weight and stability as to be unsuitable for many applications, particularly in the drug or pharmaceutical field.

It is therefore an object of the present invention to provide a microparticulate material, and a method for making such a material, which may be used as a carrier for other materials, such as pharmaceuticals.

Another object of this invention is to provide a microparticulate material into or from which other materials may selectively and controllably diffuse.

A more specific object of the present invention is to provide a sustained release pharmaceutical dosage form which may be injected intravenously.

SUMMARY OF INVENTION AND PREFERRED EMBODIMENTS

Briefly, the present invention is a microparticulate material comprised of the reaction product produced in a finely dispersed emulsion of a water immiscible solution of (a) an organic polyfunctional Lewis base, in a (b) low boiling point, polar, organic solvent, and an aqueous solution of a (c) partially hydrophilic, partially lipophilic, polyfunctional Lewis acid.

Suitable acidic materials (c) which have been found to be useful in this invention are:

Azar
Acacia Gum,
Arabic Acid,
Carboxymethylcellulose,
Ghatti Gum,
Guar Gum,
Methylcellulose,
Oxidized Cellulose,
Pectin,
Tragacanth,
Polyethylene Gylcol Suitable polar solvents (b) found useful are:

Bromoform,
Chloroform,
Dichloromethane,
Dichloroethane,
Diethyl ether,
Diisopropyl ether,
Methyl ethyl ketone
Nitrobenzene As basic materials (a), the following have been used:

monofunctional amines
Hexylamine
Isopentylamine
N-Methylpiperidine
Piperidine
difunctional amines
Dimethylethylenediamine
Hexanediamine
Piperazine
Triethylenediamine
Ethylenediamine
polyfunctional amines
Hexamethylrosanilinium cation as chloride
Rosanilinium cation as chloride
Tetramethylrosanilinium cation as chloride
Melamine
Tetraethylpentamine
Triethyltetramine Preferably, a solution of a polyamine, such as piperazine, triethylenediamine, or ethylenediamine, in chloroform, is added to an aqueous solution of a vegetable gum, such as acacia, with rapid stirring to produce a finely dispersed emulsion. The severity and time of stirring will determine the droplet size of emulsion particles and ultimately the particle size of the microparticulate product. A material for which the microparticulate product is to serve as a carrier is also included in the organic phase of the mixture. Such a material must of course be substantially non-reactive with the other components in the reaction media and must also be substantially immiscible in the aqueous phase and soluble in the organic phase. For purposes of release of such material it must also be of such molecular size that it will be able to diffuse out of the individual microspheroids of the microparticulate material.

DETAILED DESCRIPTION OF INVENTION

In each organic phase droplet of this finely dispersed emulsion the polyfunctional Lewis base is drawn to the surface of the droplet by the polar attraction of the surrounding aqueous phase. In the aqueous phase, the partially hydrophilic, partially lipophilic, polyfunctional Lewis acid is drawn, due to its partially lipophilic characteristic, toward the interface between the organic droplet and the surrounding aqueous phase where it reacts, presumably through dipole and/or ionic bonding, with the polyfunctional Lewis base concentrated on the outer surfaces of the organic phase droplets adjacent the interface, to produce a shell-like, insoluble particle generally corresponding in shape and size to the organic droplets. Each of these shell-like particles is thought to consist of an open network, or lattice, of molecules of a dipole and/or ionic salt.

This reaction, which is thought to be a two-step reaction sequence resulting in the formation of anisotropic salt films in small spherical or sphere-like shapes sometimes referred to as microspheroids, is hypothesized to proceed as follows (using piperazine arabate as a typical wall-material for purposes of this example).

1. A polyfunctional acidic macromolecule (arabic acid) protonates the nucleophilic center(s) of a base (piperazine) to form a polycarboxylic acid salt, i.e.

The polyfunctional acidic macromolecule arabic acid is dissolved in water and allowed to interact at an emulsion interface with bi-functional piperazine dissolved in chloroform; a multiple salt, piperazine arabate, forms. In this multiple salt many carboxyl groups of arabic acid (but not necessarily all of them) protonate the nucleophilic centers of piperazine and the oppositely charged ions thus formed attract one another.

2. The slightly polar non-aqueous solvent (chloroform) solvates the ion pair. The solvent serves to mask the relatively high charge density associated with the ion-pair and renders these regions compatible with the bulk phase of the non-aqueous solvent, which then attracts the solvated ion pair into its interior, i.e., Piperazine is initially dissolved in the slightly polar electrophilic solvent chloroform and the anionic portions of the ion-pair are solvated by the asymmetric solvent chloroform so as to mask the relatively high charge density associated with the anionic surface. Thus, the solvated ion-pair presents to the bulk of the chloroformic phase a relatively less polar structure and the chloroformic phase then attracts the ion pair into its interior. This solvation of the anionic centers of each ion-pair orients the pair toward the interior of the non-aqueous phase and thus orients the regions of high charge density away from the aqueous phase. Thus anisotropically oriented, there is relatively little opportunity for hydration of the charged centers and thus piperazine arabate, which should be water-soluble, does not enjoy the opportunity to dissolve.

In contrast, if the piperazine is initially dissolved in a non-polar solvent such as cyclohexane, both portions of the ion-pair, piperazine arabate, produced by the reaction are repelled from the non-polar solvent and are attracted to and hydrated by the highly polar molecules of the aqueous phase. Under such circumstances, the piperazine arabate dissolves in the aqueous phase without forming a continuous salt film or wall-like structure at the interface.

On the other hand, if piperazine is initially dissolved in a slightly polar nucleophilic solvent such as diethyl ether, the cationic portions of the ion pair formed by the reaction are solvated by the asymmetric solvent diethyl ether so as to mask the relatively high charge density associated with the cationic surface. Thus, the solvated ion-pair presents to the bulk of the ether phase a relatively less polar structure and the ether phase then attracts the ion-pair into its interior. This solvation of the cationic portions of each ion-pair orients the pair toward the interior of the non-aqueous phase and thus orients the regions of high charge density away from the aqueous phase. Thus, anisotropically oriented, there is very little opportunity for hydration of the charged centers and thus piperazine arabate, which should be water-soluble, does not enjoy the opportunity to dissolve.

The role of the non-aqueous manufacturing solvent in solvating the ion-pair is thus seen to be critical in film or wall formation. Without the orienting force provided by the polar non-aqueous solvent, during formation, the microcapsular polysalt films (walls) are more isotropic and more subject to rapid dissolution.

Once the polyfunctional salt is oriented as an anisotropic film, the stabilizing role of the non-aqueous manufacturing solvent may be taken over by non-volatile core material of appropriate polarity and the manufacturing solvent may be removed by evaporation.

As a generalization based on the dipole moments of the polar solvents listed above which may be used in the present invention and of other solvents which have not been found to be useful and on tests of graded molefractions of mixed solvents comprising chloroform with the non-polar solvent hexane, a solvent dielectric constant (as an indication of degree of polarity) of no less than 4 Debye units is thought to be necessary in the present invention.

After the reaction of the present invention is complete the phases are separated. The organic phase includes a multiplicity of shell-like structures, each enclosing solvent, residual unreacted polyfunctional Lewis base, and any foreign material incorporated in the organic phase, such as a pharmaceutical for which the microparticulate product is to act as a carrier. This organic phase, after separation, may be washed with water which is then separated by decantation. The remaining solvent, particularly if it is a low molecular weight, low boiling solvent such as chloroform, may then be removed by evaporation by drying in air or under reduced pressure.

The product of this process is a non-agglomerating, microparticulate material of very small dimensions. As pointed out above, the particle size dimensions are controlled primarily by the degree of dispersion of the emulsified reaction media or more specifically by the droplet size of the organic phase in the emulsified reaction media.

Further, because of the lattice-like nature of the reaction product forming the shell of the microspheroids, other compounds may be selectively and controllably diffused through the particle walls of the microparticulate material of the present invention or conversely prevented from diffusing through these walls. This is controlled by the particle or molecular size of the other compound and the openness of the lattice or network of molecules comprising the particle walls.

The latter factor is controlled primarily by the spacing of reactive sites on the high molecular weight polyfunctional Lewis acid and on the thickness of the particle walls.

With respect to the spacing of reactive sites on the polyfunctional Lewis acid, acacia, for example, is thought to have an average distance equivalent to the spacing of about 30 carbon atoms in a normal carbon chain between its reactive carboxyl substituents. With oxidized cellulose, this spacing may be varied, depending on the degree of oxidation; it may be equivalent to the distance between as few as 4 or as many as 100 carbon atoms in a normal carbon chain. For ready diffusion of most compounds, the spacing between cross linking sites should probably be not less than the equivalent length of a 20 carbon chain; while in order to retain most materials, the distance between reactive sites should probably not exceed a maximum on the order of the equivalent of a 360 carbon chain. Preferably the spacing is less than the equivalent of a 240 carbon chain. In this regard, it should be noted that lattice structures which are too open may be undesirable because they will admit, into the microspheroids, agents which may react with, neutralize or denature the material carrier therein. For example in an intravenously injectable sustained release dosage form, blood plasma must be excluded from the microspheroid since it will denature many pharmaceuticals.

Acacia and piperazine typify the reactants which produce a semi-permeable lattice shell, within the above preferred range of openness, through which a pharmaceutical may be released while blood plasma is excluded from the microspheroid.

The second factor affecting diffusivity from the microparticulate material is the wall thickness of the shell-like structure. This may be controlled by the concentration of the polybasic and polyacidic compounds in the reaction media and by the time of reaction. Practically speaking, it is preferable to determine a concentration of these reactants which will produce the desired particle wall thickness and to permit the reactants to substantially complete their reaction. For some purposes, however, it may be desirable to use a greater than necessary concentration of reactants, separating the phases prior to the time the reaction is substantially complete.

With respect to the Lewis base, in order to be effective in producing the microparticulate material of the present invention, this compound should have a relative basic strength, i.e., $pK_a$, on the order of 7–12. The function of this basic material is to react with reactive substituents in the structure of the polyfunctional Lewis acid, in effect orienting and interweaving, by dipole or ionic bonding, various molecules of the Lewis acid and producing a network or lattice type molecule of somewhat higher molecular weight than the original acid material. Specific known Lewis bases which may be used in the present invention are listed above in the "Summary" of this invention. Generally, these are mono, di- and poly-functional primary, secondary and tertiary amines.

It should be noted that while the hexa- and tetramethylrosanilinium cations include nitrogen functions with a formal valence of +4, these are quaternary immonium compounds and they also include at least one tertiary amino-group.

With reference to the previous theoretical description of how the reaction of this invention proceeds, it may be noted that the highly hydrophilic hydroxyl groups of arabic acid and like materials prevent the complete extraction of piperazine arabate ion-pair, so that piperazine arabate formed at the interface exists as an anisotropic film stabilized by the opposing forces of solvation, chloroform solvated carboxylate anions being attracted to the interior of the non-aqueous phase; water-solved hydroxyl groups being attracted to the interior of the aqueous phase.

This tendency to form incompletely extractably ion-pairs appears to be roughly proportional to the relative basicity of the organic cations employed and is reminiscent of Higuchi's mathematical description of the extraction properties of ion-pairs consisting of large cations and small anions (T. Higuchi et al., Anal. Chem. 39, 974 (1967).

The Lewis acid compound used in the present invention must be partially hydrophilic, in order to be soluble in the aqueous phase, and partially lipophilic, to be attracted to the interface with the organic droplets. Further, this acid must be polyfunctional, in order to be multiply oriented to the interface by the Lewis base reactant. Usually, but not necessarily insofar as the invention is presently understood, the acid is a polymerized, high molecular weight compound comprised of carbon and carbon-oxygen chains, which forms a colloidal solution in water. The spacing of the acid reactive substituents thereof may be important for purposes of diffusibility, as pointed out above. Known compounds within the foregoing definition are listed above in the Summary section of this application.

Of those listed, ghatti gum with a molecular weight averaging about 12,000 mass units and arabic acid with a molecular weight ranging from 10,000 to 20,000 mass units represent the low end of the useful polymer size span for gums. Tragacanth, with a molecular weight of about 840,000 mass units, is the largest polymer which has been found to be useful. Guar Gum differs in degree from the other members of this group in that it has many fewer carboxyl groups and in some references is identified as a non-acidic gum.

Polyethylene gylcol has been shown to be useful as the hydrophilic polymer component in the present invention in the molecular weight ranges averaging 1000, 4000, 6000 and 20,000.

As mentioned above, one of the primary uses of the microparticulate material of the present invention is as a carrier for a pharmaceutical which may be introduced into the body in any of a variety of ways, including intravenously, after which the pharmaceutical is gradually released from the microparticulate material into the body. This constitutes a new sustained release dosage form. With respect particularly to intravenous injection, this dosage form has the important advantage that it may circulate throughout the body in the blood stream relatively quickly. It should be noted that no sustained release dosage form for intravenous injection has previously been known. Further, it is particularly effective in that it prevents denaturization of the pharmaceutical agent and is not known to have any adverse side effects. For intravenous injection, the maximum particle size is generally 7 microns or below, roughly the size of the red blood cells. A maximum particle size as small as 2 microns is easily obtainable and may be desired in some cases.

Where the microparticulate material of the present invention is intended for use as a sustained release pharmaceutical carrier, the usual precautions as to sterility and non-pyrogenicity must be observed. The preferred Lewis base material for this application of the present invention is piperazine because of its known non-pyrogenicity in the body.

Following is a description of one example of the process of the present invention for making the microparticulate product taught herein. A solution of 10 grams of finely divided acacia powder (USP) in 50 cubic centimeters of distilled water and a second solution of 0.05 grams of anhydrous piperazine and 50 cubic centimeters of chloroform are prepared at room temperature. To the latter solution is added 100 milligrams of a selected drug, namely Quinacrine HCl. While stirring the acacia vigorously with a magnetic stirrer, the chloroform solution is added slowly and steadily so that the chloroform solution is emulsified in the aqueous solution. Stirring is continued for about 3 minutes to produce emulsion droplets about 5 microns in diameter. The organic phase, now consisting of emulsified microspheres, is then allowed to settle to the bottom of the container and the supernatant clear, aqueous layer is decanted. The organic phase is then washed with water to remove excess chloroform, piperazine and acacia. On exposure to the atmosphere, the microspheres lose their chloroform by evaporation leaving a microparticulate material comprised of microspheroids made up of wrinkled, continuous shell-like films, surrounding the drug, Quinacrine HCl.

Such a microparticulate material has been injected directly into the bloodstream of a frog and circulation of the microspheroids in the blood stream of the frog has been proven by microscopic observation of these microspheroids subsequently flowing in the capillary network of the web of the frog's foot. No adverse effect on the frog was observed. The sustained release of drug from the microparticulate material has been observed generally in dogs in vivo and has been studied in detail in vitro. The continuted circulation of intravenously injected radionuclide-bearing microparticles has, in separate experiments, been demonstrated in rats.

We claim:

1. Microparticulate material, consisting essentially of the ionically bonded reaction product of an emulsion of a. a water immiscible solution of piperazine, and b. an aqueous solution of a partially hydrophilic, partially lipophilic, polyfunctional Lewis acid selected from the group consisting of acacia gum, arabic acid, carboxymethyl-cellulose, ghatti gum, guar gum, methylcellulose, oxidized cellulose, pectin, tragacanth, polyethylene glycol and agar, and wherein said water immiscible solution comprises, as the solvent thereof, a polar solvent having a dielectric constant of no less than 4 Debye units.

2. Microparticulate material, consisting essentially of the ionically bonded reaction product of an emulsion of a. a water immiscible solution of a Lewis base, and b. an aqueous solution of acacia, wherein said Lewis base is selected from the group consisting of hexylamine, isopentylamine, n-methylpiperidine, piperidine, dimethylenediamine, hexanediamine, piperazine, triethylene diamine, ethylenediamine, hexamethylrosanilium cation, rosanilium cation, tetramethylrosanilium cation, melamine, tetraethylpentamine and triethyltetramine, and wherein said water immiscible solution comprises, as the solvent thereof, a polar solvent having a dielectric constant of no less than 4 Debye units.

3. Microparticulate material, as recited in claim 2, wherein said solvent is chloroform and said base is piperazine.

4. Microparticulate material, consisting essentially of the ionically bonded reaction product of an emulsion of a. a water immiscible solution of a Lewis base, and b. an aqueous solution of a partially hydrophilic, partially lipophilic, polyfunctional Lewis acid, wherein said Lewis base is selected from the group consisting of hexylamine, isopentylamine, n-methylpiperidine, piperidine, dimethylethylenediamine, hexanediamine, piperazine, triethylene diamine, ethylenediamine, hexamethylrosanilium cation, rosanilium cation, tetramethylrosanilium cation, melamine, tetraethylpentamine and triethyltetramine, and said Lewis acid is selected from the group consisting of acacia gum, arabic acid, carboxymethylcellulose, ghatti gum, guar gum, methylcellulose, oxidized cellulose, pectin, tragacanth, polyethylene glycol and agar, wherein said water immiscible solution comprises, as the solvent thereof, a polar solvent having a dielectric constant of no less than 4 Debye units, and wherein said microparticulate material further includes, entrapped in said reaction product, a material essentially non-reactive with the reactants and reaction product therein and which is diffusible through said reaction product.

5. Microparticulate material, as recited in claim 4, wherein said entrapped material has pharmaceutical activity.

6. A method of producing a microparticulate material, said method comprising a. adding to an aqueous solution of a partially hydrophilic, partially lipophilic, polyfunctional Lewis acid, a water immiscible solution of a Lewis base, b. maintaining said solutions in an agitated condition during and after the mixing thereof, c. separating and washing the water immiscible phase, and d. removing any remaining solvent in said water immiscible phase, wherein said polyfunctional Lewis acid is selected from the group consisting of acacia gum, arabic acid, carboxmethylcellulose, ghatti gum, guar gum, methylcellulose, oxidized cellulose, pectin, tragacanth, polyethylene glycol and agar, and said polyfunctional Lewis base is selected from the group consisting of hexylamine, isopentylamine, N-methylpiperidine, piperidine, dimethylethylenediamine, hexanediamine, piperazine, triethylene diamine, ethylenediamine hexamethylrosanilinium cation, rosanilinium cation, tetramethylrosanilinium cation, melamine, tetraethylpentamine and triethyltetramine, and said water immiscible solution comprises, as the solvent thereof, a polar solvent having a dielectric constant of no less than 4 Debye units.

7. Method, as recited in claim 6, wherein said solvent is selected from the group consisting of bromoform, chloroform, dichloromethane, dichloroethane, diethyl ether, diisopropyl ether, methyl ethyl ketone and nitrobenzene.

8. Method, as recited in claim 6, wherein said solvent is chloroform.

9. Method, as recited in claim 6, wherein said polyfunctional Lewis base is piperazine.

10. Method, as recited in claim 6, wherein said polyfunctional Lewis acid is acacia.

* * * * *